US012097075B2

(12) United States Patent
Alizad et al.

(10) Patent No.: US 12,097,075 B2
(45) Date of Patent: Sep. 24, 2024

(54) ULTRASOUND SYSTEMS AND METHODS USING MASS CHARACTERISTIC FREQUENCY

(71) Applicant: Mayo Foundation for Medical Education and Research, Rochester, MN (US)

(72) Inventors: Azra Alizad, Rochester, MN (US); Mostafa Fatemi, Rochester, MN (US); Juanjuan Gu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 17/466,073

(22) Filed: Sep. 3, 2021

(65) Prior Publication Data

US 2022/0142613 A1 May 12, 2022

Related U.S. Application Data

(60) Provisional application No. 63/074,020, filed on Sep. 3, 2020.

(51) Int. Cl.
*A61B 8/08* (2006.01)
*A61B 8/00* (2006.01)

(52) U.S. Cl.
CPC .......... *A61B 8/5215* (2013.01); *A61B 8/0825* (2013.01); *A61B 8/085* (2013.01); *A61B 8/485* (2013.01); *A61B 8/4488* (2013.01)

(58) Field of Classification Search
CPC ..... A61B 8/0825; A61B 8/085; A61B 8/4488; A61B 8/485; A61B 8/5215
See application file for complete search history.

(56) References Cited

U.S. PATENT DOCUMENTS

2016/0018364 A1* 1/2016 Rosenzweig ...... G01N 29/4472
73/597

FOREIGN PATENT DOCUMENTS

CN 103800038 * 5/2014

OTHER PUBLICATIONS

Translated CN 103800038 (Year: 2014).*
Gruber, I. et al., BMC Cancer 2013, 13:328, p. 1-8.
Li, C. et al., Ultrasound Med Biol. Oct. 2009; 35(10), p. 1615-1628.
Youk, Ji et al., Ultrasonography 36(4), Oct. 2017, p. 300-309.

* cited by examiner

*Primary Examiner* — Katherine L Fernandez
*Assistant Examiner* — Brooke Lyn Klein
(74) *Attorney, Agent, or Firm* — Quarles & Brady LLP (57) ABSTRACT

Ultrasound systems and methods are provided using mass characterization frequency methods that provide for predicting benign or malignant lesions, a response to treatment, tumor grading, and/or the expressions of immunohistochemical biomarkers, which are currently used for breast cancer classification and hormone therapy determination. The systems and methods are based on the shear wave parameter, mass characteristic frequency. The status of malignancy, treatment response, grade, and/or each immunohistochemical biomarker may be determined based on a corresponding mass characteristic frequency threshold.

21 Claims, 7 Drawing Sheets

ULTRASOUND SYSTEMS AND METHODS USING MASS CHARACTERISTIC FREQUENCY

CROSS-REFERENCE TO RELATED APPLICATIONS

This application claims the benefit of U.S. Provisional Patent Application Ser. No. 63/074,020 filed on Sep. 3, 2020 and entitled "Ultrasound Methods Using Mass Characteristic Frequency for Prediction of Invasive Breast Cancer," which is incorporated herein by reference as if set forth in its entirety for all purposes.

STATEMENT REGARDING FEDERALLY SPONSORED RESEARCH

This invention was made with government support under CA148994 awarded by the National Institutes of Health. The government has certain rights in the invention.

BACKGROUND

Breast cancer is a complex and heterogeneous disease at the molecular level, and is divided into various subtypes. Intra-tumor heterogeneity, diverse molecular and phenotypical profiles within the same tumor are associated with poor prognosis, leading to therapeutic resistance and treatment failure. The advantages of assessing prognostic and predictive factors are becoming increasingly apparent. In addition to the evaluation of histologic subtypes, statuses of immunohistochemical (IHC) biomarkers, usually obtained from core biopsies, or from the surgical specimen, include estrogen receptor (ER) status, progesterone receptor (PR) status, human epidermal growth factor receptor 2(HER2) status and Ki-67 proliferation index, and are used for subtype classification. In addition to histological subtype and biomarkers, histological grade, lymph node involvement and mass size are also important prognostic factors. Expressions of ER and PR are used to determine if the patient should be recommended hormone therapy. HER2 over-expression indicates a poorer prognosis and these tumors may benefit from targeted anti-HER2 therapy. Elevated Ki-67 proliferation index is a negative prognostic factor. However, the results of these biomarker assays from core needle biopsy might be different from the result on surgical excision due to the tumor heterogeneity or sampling errors. Thus, additional quantitative imaging of the breast could add useful information to that obtained from the core biopsies. Correlation between tumor stiffness and aggressive biology of breast cancer has been studied and findings indicate that stiffness regulates pro-metastatic behaviors of cancer and corresponds with tumor progression and metastasis. Quantitative estimation of tumor stiffness can potentially add useful information similar to the prognostic features of heterogeneous breast carcinoma.

Shear wave elastography (SWE) is a new emerging technique in breast cancer diagnosis by measuring the tissue stiffness. Generally, malignant lesions are stiffer than the benign lesions. Mean, maximum, minimum shear wave elasticity and standard deviation of the shear wave elasticity distribution inside the lesion are available on the commercial SWE machines for lesion characterization. Moreover, the ratio of the longest dimension of the lesion on elasticity imaging to the longest dimension on B-mode imaging is also used. SWE is a qualitative and quantitative method for measuring tissue stiffness with high reproducibility. It has been shown that adding SWE to the clinical ultrasound can greatly improve the specificity for differentiating malignant lesions from benign lesions as malignant lesions are stiffer than benign lesions. SWE has been further correlated with prognostic factors of breast carcinoma, but results were not consistent among different studies.

Some SWE studies didn't observe any statistically significant correlation of lymph node involvement and histological grade with SWE parameters. Moreover, some studies found that it was not possible to correlate the mean shear wave elasticity value with ER, PR, Ki-67 and HER2 statuses. Therefore, solid conclusions were not reached about the relationship between SWE parameters and prognostic factors that could potentially benefit breast cancer treatment and thus improve outcome. Though not all studies showed the same relationships between the SWE parameters and breast cancer prognostic factors, generally, higher shear wave elasticity values showed significant association with poorer prognostic factors of invasive breast cancer and a lower survival rate when compared to those with lower shear wave elasticity values.

Though shear wave parameters are useful in differentiating benign lesions from malignant lesions, the correlation between tumor stiffness and tumor aggressiveness is still being investigated. Previous approaches based on these shear wave parameters have not achieved satisfactory performance in breast invasiveness prediction.

SUMMARY OF THE DISCLOSURE

The present disclosure addresses the aforementioned drawbacks by providing systems and methods for determining the relationship between SWE parameters and prognostic factors, and the statuses of biomarkers. In some configurations, a shear wave parameter of mass characteristic frequency $f_{mass}$, may be determined and correlated with prognostic histologic features and IHC biomarkers. Prognostic factors may include mass size, lymph node involvement status, presence of calcifications, histologic type, histologic grade, and the like. Biomarkers may include ER, PR, HER2, Ki-67, and the like.

In one configuration, a method is provided for determining expression of a biomarker in a region of interest of a subject. The method includes accessing shear wave data acquired from the region of interest of the subject using an ultrasound imaging system that includes shear wave speed data and determining a minimum shear wave speed from the shear wave speed data. The method also includes accessing image data from the region of interest of the subject and determining a physical parameter of the region of interest from the image data. The method also includes determining a mass characterization frequency based on a ratio of the determined minimum shear wave speed and the determined physical parameter of the region of interest. The method also includes generating a report of expression of the biomarker in the region of interest based on the determined mass characterization frequency.

In one configuration, a system is provided for determining expression of a biomarker in a region of interest of a subject. The system includes an ultrasound imaging system configured to acquire image data and shear wave data from the region of interest of the subject. The shear wave data includes shear wave speed data. The system also includes a computer system configured to access the acquired shear wave data acquired from the region of interest of the subject and determine a minimum shear wave speed from the shear wave speed data. The computer system is also configured to access the image data from the region of interest of the subject and determine a physical parameter of the region of interest from the image data. The computer system is also configured to determine a mass characterization frequency based on a ratio of the determined minimum shear wave speed and the determined physical parameter of the region of interest. The computer system is also configured to generate a report of expression of the biomarker in the region of interest based on the determined mass characterization frequency.

In one configuration, a method is provided for determining a response to chemotherapy treatment in a region of interest of a subject. The method includes accessing shear wave data acquired from the region of interest of the subject using an ultrasound imaging system that includes first shear wave speed data acquired before administration of treatment and determining a first minimum shear wave speed from the first shear wave speed data. The method also includes accessing first image data from the region of interest of the subject acquired before administration of treatment and determining a first physical parameter of the region of interest from the first image data. The method also includes determining a first mass characterization frequency based on a ratio of the determined first minimum shear wave speed and the determined first physical parameter of the region of interest. The method also includes accessing shear wave data acquired from the region of interest of the subject using the ultrasound imaging system that includes second shear wave speed data acquired after administration of treatment and determining a second minimum shear wave speed from the second shear wave speed data. The method also includes accessing second image data from the region of interest of the subject acquired after administration of treatment and determining a second physical parameter of the region of interest from the second image data. The method also includes determining a second mass characterization frequency based on a ratio of the determined second minimum shear wave speed and the determined second physical parameter of the region of interest. The method also includes generating a report of a response to treatment in the region of interest based on a comparison of the determined first mass characterization frequency and the second mass characterization frequency.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention. Like reference numerals will be used to refer to like parts from Figure to Figure in the following description.

DETAILED DESCRIPTION

Systems and methods are provided for determining the relationship between SWE parameters and prognostic factors, and the statuses of biomarkers. In some configurations, a shear wave parameter of mass characteristic frequency $f_{mass}$, may be determined and correlated with prognostic histologic features and immunohistochemical (IHC) biomarkers. Prognostic factors may include mass size, lymph node involvement status, presence of calcifications, histologic type, histologic grade, and the like. Biomarkers may include estrogen receptor (ER), progesterone receptor (PR), human epidermal growth factor receptor 2 (HER2), proliferation marker Ki-67, and the like.

The relationship between SWE parameters and breast cancer prognostic factors may be determined in accordance with the present disclosure using a determination of mass characteristic frequency. Parameters such as large invasive size, positive axillary lymph node, invasive histological subtypes, and high histological grade may be correlated with high elasticity values (such as $E_{mean}$ and $E_{max}$) and strong stiffness heterogeneity (such as $E_{sd}$).

In some configurations, a mass characteristic frequency is determined based on a ratio of shear wave speed and a physical parameter of a region of interest. The region of interest may include a tumor, mass, lesion, cancer, breast mass, breast lesion, breast cancer, and the like. Mass characteristic frequency may be defined as the ratio of the minimum shear wave speed ($V_{min}$) in the region of interest, such as a breast mass, to the physical parameter size, such as mass size, (d). $V_{min}$ may be obtained from shear wave elastography imaging. The physical parameter size d may be determined as the greatest dimension of the region of interest, such as a tumor or mass, shown on an ultrasound image, such as a B-mode image. In a non-limiting example, the region of interest is a breast mass and the physical parameter d is the greatest dimension of the tumor shown on an ultrasound image. In a non-limiting example, the ratio of minimum shear wave speed to the physical parameter includes dividing the minimum shear wave speed by the physical parameter value. Mass characteristic frequency may be correlated with breast cancer prognostic factors and IHC biomarker expressions. In some configurations, cut-offs of $f_{mass}$ may be used for the determination of the statuses of IHC biomarkers. The breast cancer invasiveness and treatment plan may be further determined based on the expressions of the IHC biomarkers.

In some configurations, the inverse of the mass characteristic frequency may be determined. The inverse of the mass characteristic frequency is the mass transit time, and may be used in the same manner as the mass characteristic frequency. In some configurations, the square root of the mass characteristic frequency may be used. In some configurations, when determining the mass characteristic frequency the minimum shear wave speed may be replaced with the maximum shear wave speed or the mean shear wave speed, such as in a breast mass, obtained with shear wave elastography. In some configurations, the greatest dimension of the tumor on the B-Mode image may be replaced with the equivalent circular diameter obtained from the measured mass perimeter, and the like.

One advantage of a method in accordance with the present disclosure is that the method may provide information for the entire tumor. In current conventional diagnostic methods, expressions of IHC biomarkers are obtained from core biopsies, or from a surgical specimen. However, the results of these biomarker assays from core needle biopsy might be different from the result on surgical excision due to tumor heterogeneity or sampling errors. For example, a biopsy typically only samples a small portion of a tissue region, which because of tumor heterogeneity may often provide limited information across the full tumor extent. An evaluation of the whole tumor may be less susceptible to these errors. Also, mass characteristic frequency may be obtained based on non-ionizing radiation ultrasound, which also has the advantage of being non-invasive. The cost for using methods in accordance with the present disclosure may also be much lower when compared with magnetic resonance imaging (MRI) or other conventional methods.

Larger mass size may provide a determinant of larger mean elasticity, and may be associated with poor prognostic factors of invasive breast cancer. Tumor size may also be correlated with shear wave elasticity ($E_{mean}$, $E_{max}$, $E_{min}$ and $E_{sd}$). Breast cancer patients with positive axillary lymph node (ALN) may exhibit higher stiffness in invasive breast masses. Through an ROC curve analysis, high specificities may be obtained for both the $E_{mean}$ and $E_{max}$. In some configurations, shear wave elasticity of invasive breast masses could be used for prediction of ALN metastasis.

Although the presence of cluster, coarse, or large calcifications in benign breast masses can induce apparent high stiffness in benign lesions and misdiagnosed as malignant, conventionally there is no relationship between the elasticity of invasive mass and the presence of calcifications. However, $f_{mass}$ may be correlated with the presence of calcifications. Differences may also be seen for the elasticity among different histological types and the stiffness of invasive mass. In a non-limiting example, the lobular carcinoma exhibited the highest stiffness.

Differences of SWE parameters ($E_{mean}$ and $E_{max}$) between the Grade I/II and Grade III cancers may also be exploited to determine grades. In a non-limiting example, the Grade III cancers showed a higher stiffness relative to Grade I/II cancers. It is contemplated that tumor stiffness is influenced by the combination of cellularity, microvascular density, necrosis, and fibrosis, which may contribute to the increased stiffness in high grade cancers. The abnormal extracellular matrix, which derails stromal cells and leads to tumor-associated angiogenesis and inflammation, may also be a factor for increased stiffness during tumor progression. It is contemplated also that cancer stiffness can be affected by desmoplastic reaction, which is associated with dense fibrous tissue, and is therefore more marked in low grade cancerous masses than high grade cancers.

Using IHC biomarkers, breast cancers can be divided into subtypes with strong prognostic effects. Distinguishing tumor subtypes may be useful for therapeutic management. In non-limiting examples, $E_{max}$ and $E_{sd}$ were correlated with HER2 status. Previously, no statistically significant correlation with IHC biomarkers or molecular subtypes was reported. In addition, a correlation of high stiffness values may be correlated with aggressive subtypes of breast cancer.

In accordance with the present disclosure, mass characteristic frequency may be correlated with IHC biomarker statuses (such as ER, PR, HER2, Ki-67, and the like), as well as the IHC subtypes. Mass characteristic frequency may be reported in units of frequency, such as Hertz. The physical meaning of mass characteristic frequency can be explained as the inverse of the maximum propagation time in a mass, such as in each breast mass as a non-limiting example. Mass characteristic frequency may be used for biomarker status differentiation, such as by determining threshold values between the biomarkers. In a non-limiting example, keeping the sensitivity larger than 80% resulted in the specificity for the HER2 biomarker as high as 68.1%.

In general, luminal-type tumors have a relatively good prognosis, whereas patients with triple negative (TN) tumors have a shorter and poor response to the typical endocrine therapies. In young women with genetic mutation, TN tumors often manifest as circumscribed, benign-looking masses. TN cancers and HER2+ cancers may be softer than other IHC subtypes. In previous studies, however, it was shown that TN breast cancer was the hardest subtype among the intrinsic subtypes of invasive breast cancers. Luminal subtypes may be associated with higher $f_{mass}$ values. Lower $f_{mass}$ may be seen in more aggressive types, including luminal B-like, HER2+ and TN. Thus, lower $f_{mass}$ values may indicate a poor prognostic factor.

In some configurations, an $f_{mass}$ value may be used to determine the relationship between SWE and breast cancer prognostic factors, including invasive mass size, presence of calcifications, lymph node status, histological type, histological grade, IHC biomarkers, as well as IHC subtypes. $f_{mass}$ may correlate with the presence of calcifications, lymph node status, histological grade, IHC biomarker status (ER, PR, HER2 and Ki-67) and IHC subtypes. Poor prognostic factors may also be associated with high shear wave elasticity values and low mass characteristic frequency value. In some configurations, the systems and methods in accordance with the present disclosure provide for SWE data to be used for breast cancer treatment planning.

Figure 1A:
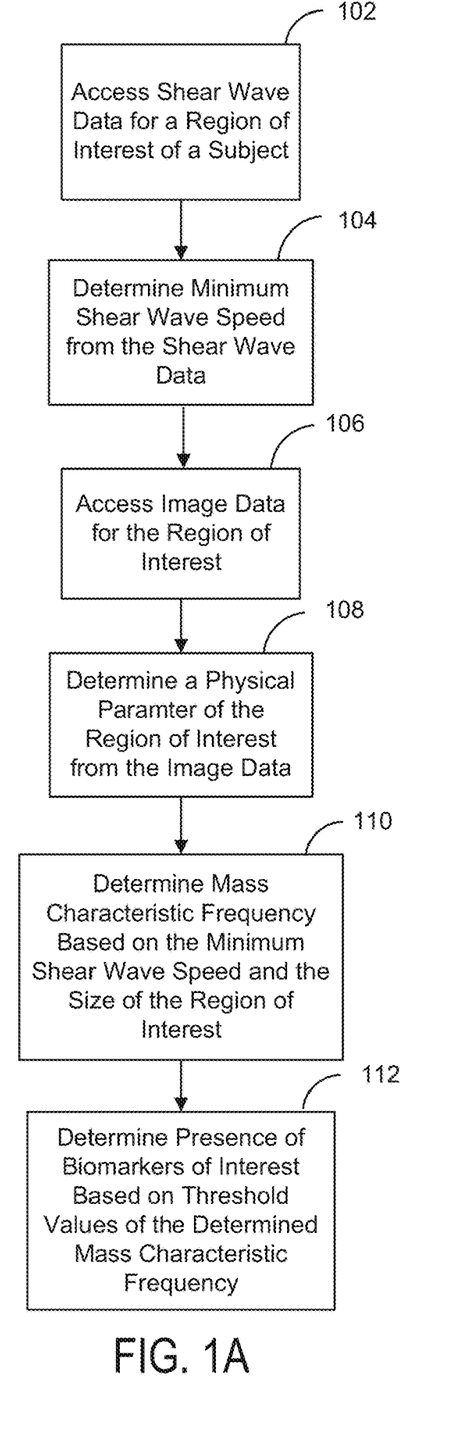
FIG. 1A shows a flowchart of non-limiting example steps for determining the presence of biomarkers of interest from a determined mass characteristic frequency.

Referring to FIG. 1A, a flowchart of non-limiting example steps for determining the presence of biomarkers of interest from a determined mass characteristic frequency is shown. Shear wave data for a region of interest of a subject may be accessed or acquired at step 102. Shear wave data may be accessed from a data repository or database, such as a medical image archive, or the shear wave data may be otherwise acquired using an ultrasound system capable of recording shear wave data. A region of interest may include a tumor or a lesion within the subject, such as a breast tumor. A minimum shear wave speed for the region of interest may be determined at step 104 from the shear wave speed data. Determining a minimum shear wave speed may include determining the speed of propagation for a plurality of shear waves through the region of interest at a plurality of locations to generate a plurality of wave speeds and determining the minimum shear wave speed for the region of interest from the plurality of shear wave speeds.

Image data for the region of interest may be accessed or acquired at step 106. Image data may include ultrasound image data, such as B-mode image data in a non-limiting example. The image data may be accessed from a data repository or database, such as a medical image archive, or the image data may be otherwise acquired using an ultrasound system, or any other medical imaging system. The physical parameter of the region of interest may be determined from the image data at step 108. In a non-limiting example, the region of interest is a breast mass or tumor, and the physical parameter is a size d that may be determined as the greatest dimension of the tumor shown on an ultrasound image, such as a B-mode image. For a non-limiting example circular or spherical tumor, the greatest dimension may be the diameter of the tumor.

A mass characteristic frequency may be determined at step 110 based on the determined minimum shear wave speed and size of the region of interest. In a non-limiting example, the mass characteristic frequency $f_{mass}$ is the ratio of the minimum shear wave speed ($V_{min}$) in a breast mass to the mass size (d).

The presence of biomarkers of the region of interest may be determined at step 112 and a report of biomarker presence or subject prognosis may be generated based on whether the mass characteristic frequency meets certain threshold value criteria. In some configurations, threshold cut-offs of $f_{mass}$ may be used for the determination of the statuses of IHC biomarkers. Breast cancer invasiveness and a treatment plan for treating the breast cancer may be further determined based on the expressions of the IHC biomarkers. Other reports or prognoses may be generated based upon the mass characteristic frequency such as, a prediction of a metastatic axillary lymph node, histological grade, differentiation of a benign breast lesion from a malignant lesion, presence of calcifications, differentiation of a benign lesion from malignant lesion in breast tissue, and the like.

Figure 1B:
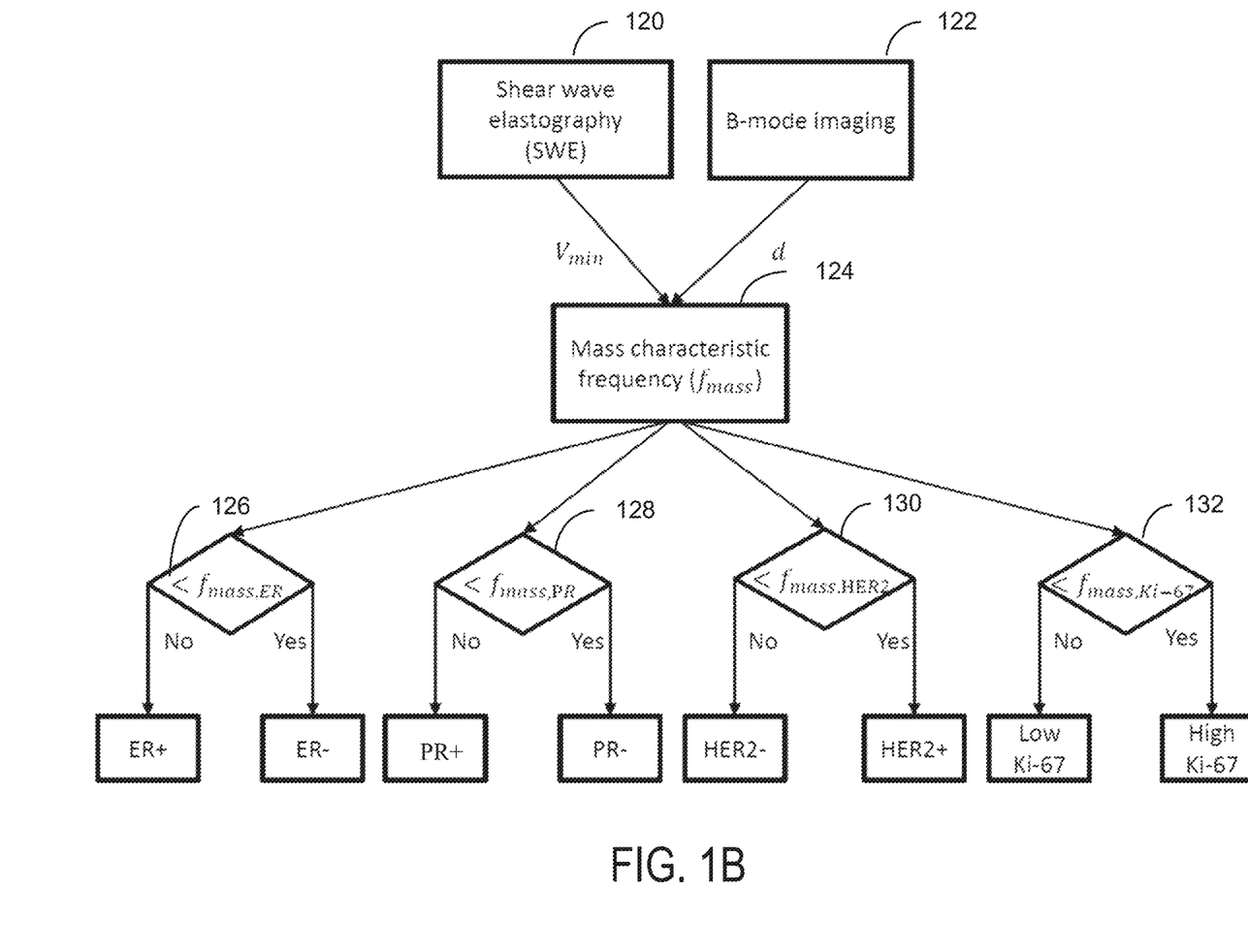
FIG. 1B shows an illustration of applying the mass characteristic frequency for immunohistochemical biomarker expression determination.

Referring to FIG. 1B, a flowchart of non-limiting example steps for determining the presence of biomarkers of interest from threshold values of a determined mass characteristic frequency is shown. In some configurations, a plurality of threshold values may be used to separate a plurality of biomarkers indicated by different values of the mass characteristic frequency. Shear wave elastography data that may provide a minimum shear wave speed ($V_{min}$) is provided at step 120. Ultrasound B-mode imaging data that may provide a dimension (d) for a region if interest is shown at step 122. The mass characteristic frequency ($f_{mass}$) may be determined based upon a ratio of $V_{min}$ and d at step 124. If $f_{mass}$ exceeds a threshold value for a biomarker, then the presence of the biomarker may be determined according to steps 126, 128, 130 and 132 for determining the presence of ER, PR, HER2, or Ki-67 respectively, as non-limiting examples.

Figure 1C:
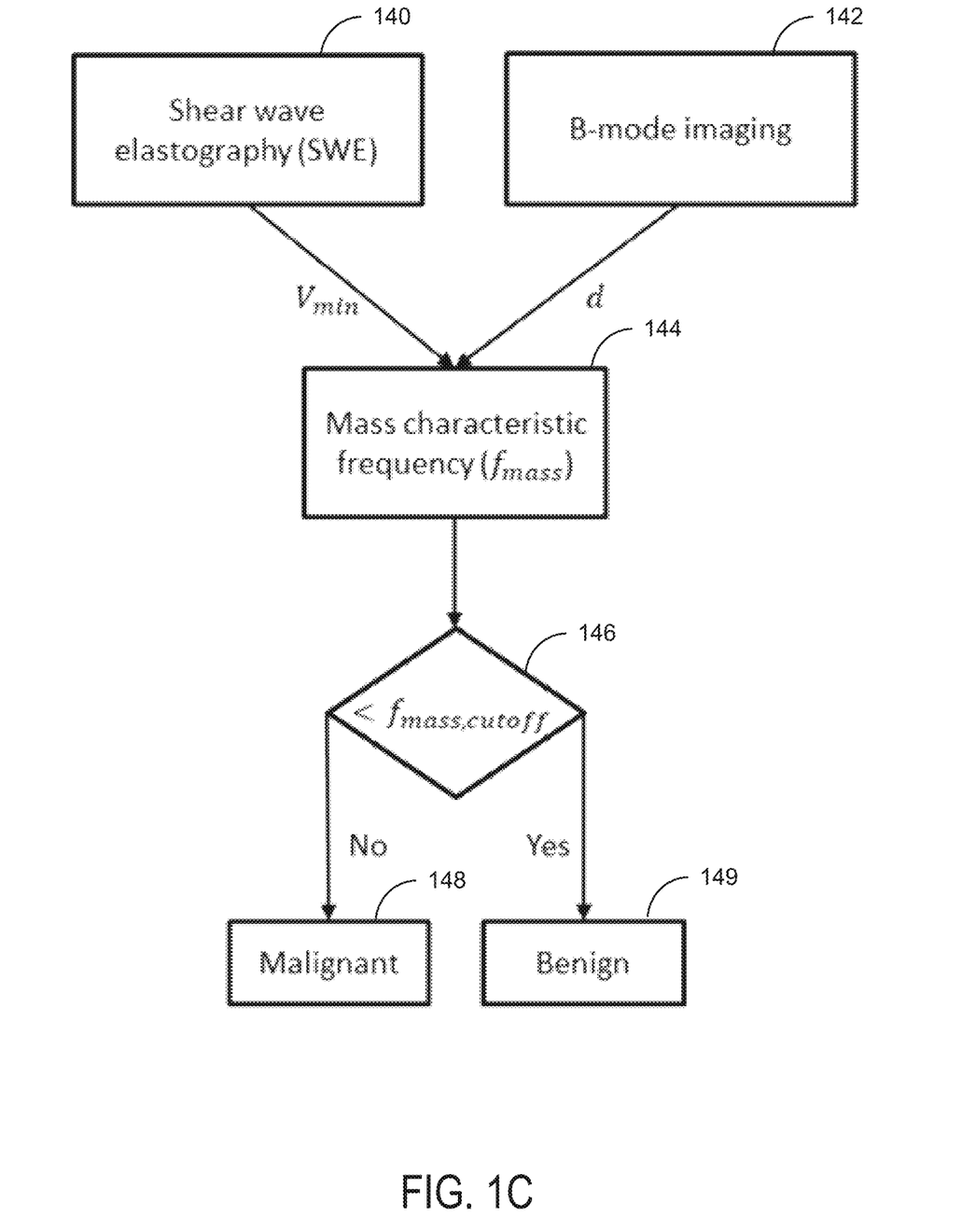
FIG. 1C shows an illustration of applying the mass characteristic frequency for determining whether a tumor or mass is benign or malignant.

Referring to FIG. 1C, a flowchart is illustrating for an example method of determining a mass characteristic frequency and, based on the determined mass characteristic frequency, classifying or otherwise determining whether a region of interest, such as a tumor or mass, is benign or malignant. Shear wave elastography data that may provide a minimum shear wave speed ($V_{min}$) are provided at step 140. Ultrasound B-mode imaging data that may provide a dimension (d) for a region of interest are shown at step 142. The mass characteristic frequency ($f_{mass}$) may be determined based upon a ratio of $V_{min}$ and d at step 144. At step 146, if the value for $f_{mass}$ is below a threshold value for determining whether the region of interest (e.g. tumor, mass, or the like) is benign or malignant, then the region of interest may be determined to be benign at step 149. If, at step 146, the value of $f_{mass}$ exceeds the threshold value for determining whether the region of interest (e.g. tumor, mass, or the like) is benign or malignant, then the region of interest may be determined to be malignant at step 148.

Breast ultrasound (US) is commonly used in the evaluation of breast lesions. However, its low specificity leads to a significant number of benign biopsies. The addition of US elastography techniques, including shear wave elastography (SWE), can advantageously provide a relative increase in specificity with US for breast cancer detection.

In a non-limiting example study, 310 benign lesions and 204 malignant lesions were assessed. The benign lesions held an average value of $f_{mass}$=157.8±94.1 Hz. The malignant lesions held an average value of $f_{mass}$=220.0±130.6 Hz. $E_{mean}$, $E_{max}$ and $f_{mass}$ were included in the analysis. The AUC was 0.888 (95% CI: 0.83-0.95). With an optimal cutoff for malignancy probability at 0.28, the sensitivity and specificity were 85.1% (0.74-0.92) and 92.0% (0.84-0.96), respectively. In a combined high-definition microvasculature imaging (HDMI) and shear wave elastography (SWE) model, NV, NB, VD, SVP, $D_{max}$, $D_{min}$, $\tau_{mean}$, $\tau_{max}$, $BA_{mean}$, $BA_{max}$, $MD_{mean}$, FD, $E_{mean}$, $E_{max}$ and $f_{mass}$ were assessed. The AUC (0.973, 95% CI: 0.95-0.99) was improved in comparison to other models. With an optimal cutoff for the malignancy probability as 0.25, the sensitivity and specificity were 95.5% (0.87-0.99) and 89.7% (0.81-0.95), respectively. Higher tumor grade was associated with higher $D_{max}$, NV, mvFD, NB and lower $f_{mass}$ values. Less aggressive subtypes, Luminal A and Luminal B (HER2-), corresponded to lower $E_{max}$, $D_{max}$, NV, NB, and higher $f_{mass}$ values. A summary of non-limiting example parameters for different malignant grades and molecular subtypes is shown in Table 1 below with the quantity of each included in the assessment in parentheses.

TABLE 1

Summary of non-limiting example parameters for different malignant grades and molecular subtypes.

| | $f_{mass}$(Hz) |
|---|---|
| Histologic Type: Benign (310) | |
| Fibroadenoma (109) | 143.0 ± 64.5 |
| Benign changes (77) | 146.4 ± 94.0 |
| Fibrocystic changes (30) | 171.1 ± 104.4 |
| Papilloma (28) | 186.7 ± 88.3 |
| PASH (22) | 139.8 ± 79.6 |
| Fat Necrosis (18) | 203.5 ± 184.1 |
| Atypical (14) | 192.3 ± 105.3 |
| Duct ectasia (6) | 231.8 ± 86.7 |
| Adenoma (4) | 99.2 ± 56.2 |
| Others (2) | 243.9 ± 71.1 |
| p value | 0.02 |
| Histologic Type: Malignant (204) | |
| IDC (136) | 212.3 ± 124.9 |
| IMC (27) | 227.8 ± 139.1 |
| ILC (24) | 241.1 ± 128.9 |
| DCIS (15) | 253.3 ± 172.6 |
| Other (2) | 97.2 ± 90.6 |
| p value | 0.48 |
| Histologic Grade | |
| I (54) | 278.5 ± 117.1 |
| II (92) | 220.6 ± 140.7 |
| III (54) | 155.6 ± 90.8 |
| p value | <.001 |
| Molecular Subtypes | |
| Luminal A (76) | 257.3 ± 120.5 |
| Luminal B HER2- (58) | 218.2 ± 139.0 |
| Luminal BHER2+ (21) | 136.2 ± 98.4 |
| HER2+ (4) | 95.5 ± 33.2 |
| TNBC (2) | 189.3 ± 85.6 |
| p value | <.001 |

Figure 1D:
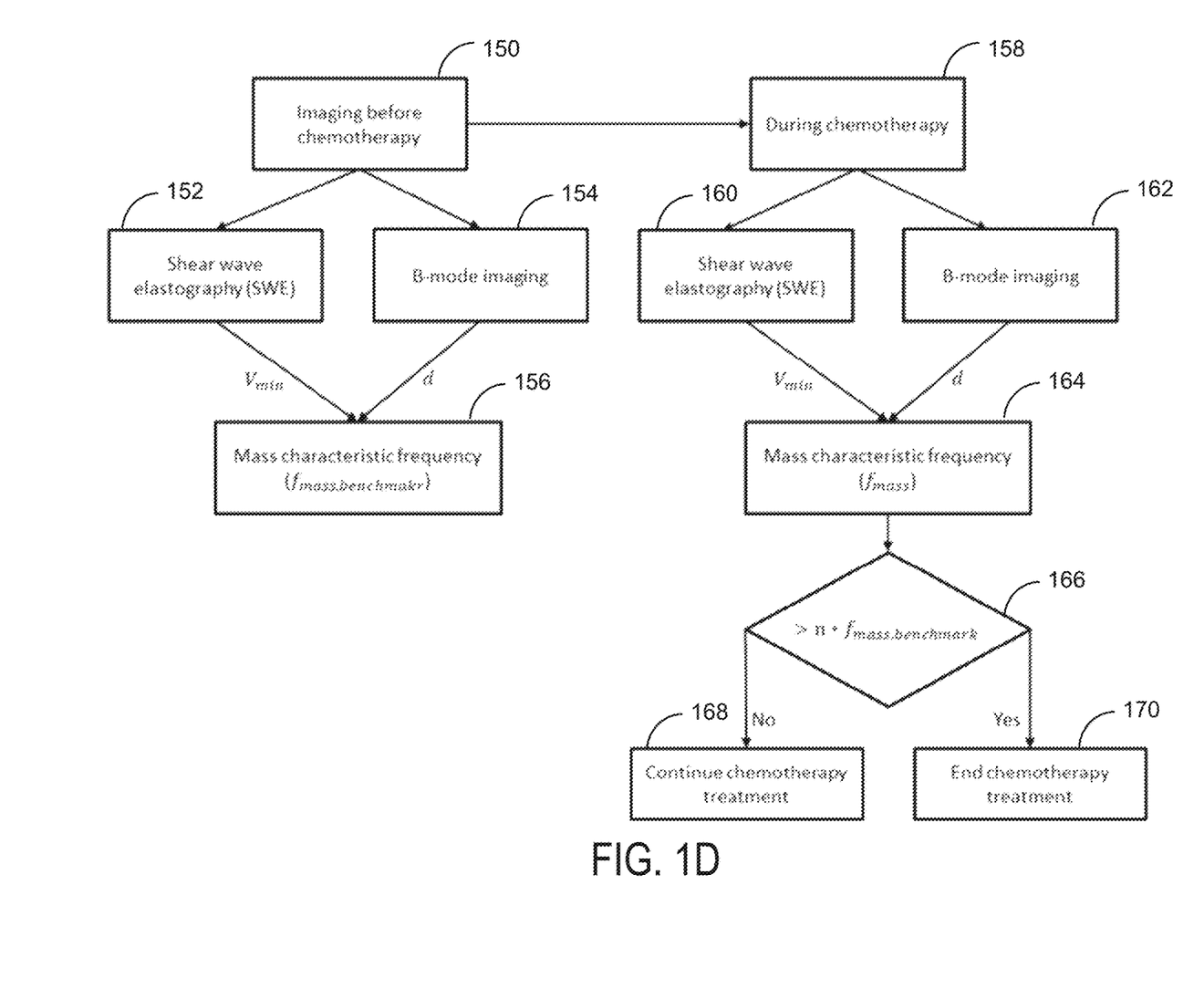
FIG. 1D shows an illustration of applying the mass characteristic frequency for monitoring a region of interest for response to a chemotherapy treatment.

Referring to FIG. 1D, a flowchart is illustrated for an example method of determining a mass characteristic frequency and, based on the determined mass characteristic frequency, monitoring a region of interest for response to a chemotherapy treatment, or other treatment provided to a subject. Imaging may be performed prior to the administration of chemotherapy or other treatment at step 150. Shear wave elastography data that may provide a minimum shear wave speed ($V_{min}$) for a region of interest, and which have been acquired before chemotherapy or other treatment have been administered to the subject, are provided at step 152. Ultrasound B-mode imaging data that may provide a dimension (d) for a region of interest, and which have been acquired before chemotherapy or other treatment have been administered to the subject, are provided at step 154. The benchmark mass characteristic frequency ($f_{mass\text{-}benchmark}$) for a region of interest before administration of chemotherapy or other treatment may be determined based upon a ratio of $V_{min}$ and d at step 156 and may provide a base value for comparison once therapy has been administered.

After or during the administration of chemotherapy or other treatment at step 158, image data may once again be acquired for the region of interest. Shear wave elastography data that may provide a minimum shear wave speed ($V_{min}$) for the region of interest (during or after chemotherapy or other treatment) may be obtained at step 160. Ultrasound B-mode imaging data that may provide a dimension (d) for a region of interest (during or after chemotherapy or other treatment) may be obtained at step 162. The mass characteristic frequency ($f_{mass}$) for a region of interest after administration of chemotherapy or other treatment may be determined based upon a ratio of $V_{min}$ and d at step 164. The determined mass characteristic frequency ($f_{mass}$) for a region of interest after administration of chemotherapy or other treatment may be compared to the benchmark mass characteristic frequency ($f_{mass\text{-}benchmark}$) for a region of interest before administration of chemotherapy or other treatment to determine what changes may have occurred during treatment at step 166. If $f_{mass}$ exceeds a threshold value of change over the benchmark mass characteristic frequency ($f_{mass\text{-}benchmark}$), then treatment may be discontinued at step 170. If $f_{mass}$ does not exceed a threshold value of change over the benchmark mass characteristic frequency ($f_{mass\text{-}benchmark}$), then treatment may be continued at step 168.

Neoadjuvant chemotherapy (NACT) is an established therapeutic strategy for operable breast cancers and locally advanced breast cancers and allows more patients to undergo breast-preserving surgery. A pathological complete response (pCR) to NACT is associated with increased disease-free interval. However, responses to NACT are quite variable. With the increased use of NACT, it is crucial to have an accurate prediction of tumor response to NACT.

In some configurations, a number of visits or chemotherapy sessions may be used to assess the response to treatment or chemotherapy. An $f_{mass}$ analysis may provide for predicting the endpoint of NACT in patients. An $f_{mass}$ analysis may also provide for personalizing the treatment regimens of patients with breast cancer receiving NACT. In non-limiting examples, treatment may be increased to achieve the desired $f_{mass}$ result, or the chemotherapy agent may be changed to an alternative chemotherapy agent to provide for the desired $f_{mass}$ result.

In a non-limiting example study, 62 female patients (age range 27-78 years) with 62 biopsy-proven invasive breast cancers were assessed. A significant difference was found in the change of the mass characteristic frequency measured between the first and the third visits ($f_{mass1\text{-}3}$, p<0.001). $E_{mean}$ and $f_{mass}$ for different molecular subtypes measured during the three visits were recorded and indicated that stiffness decreased significantly for the responders, while remained high for the non-responders. The $f_{mass}$ remained low for non-responders and increased significantly for responders.

Figure 2:
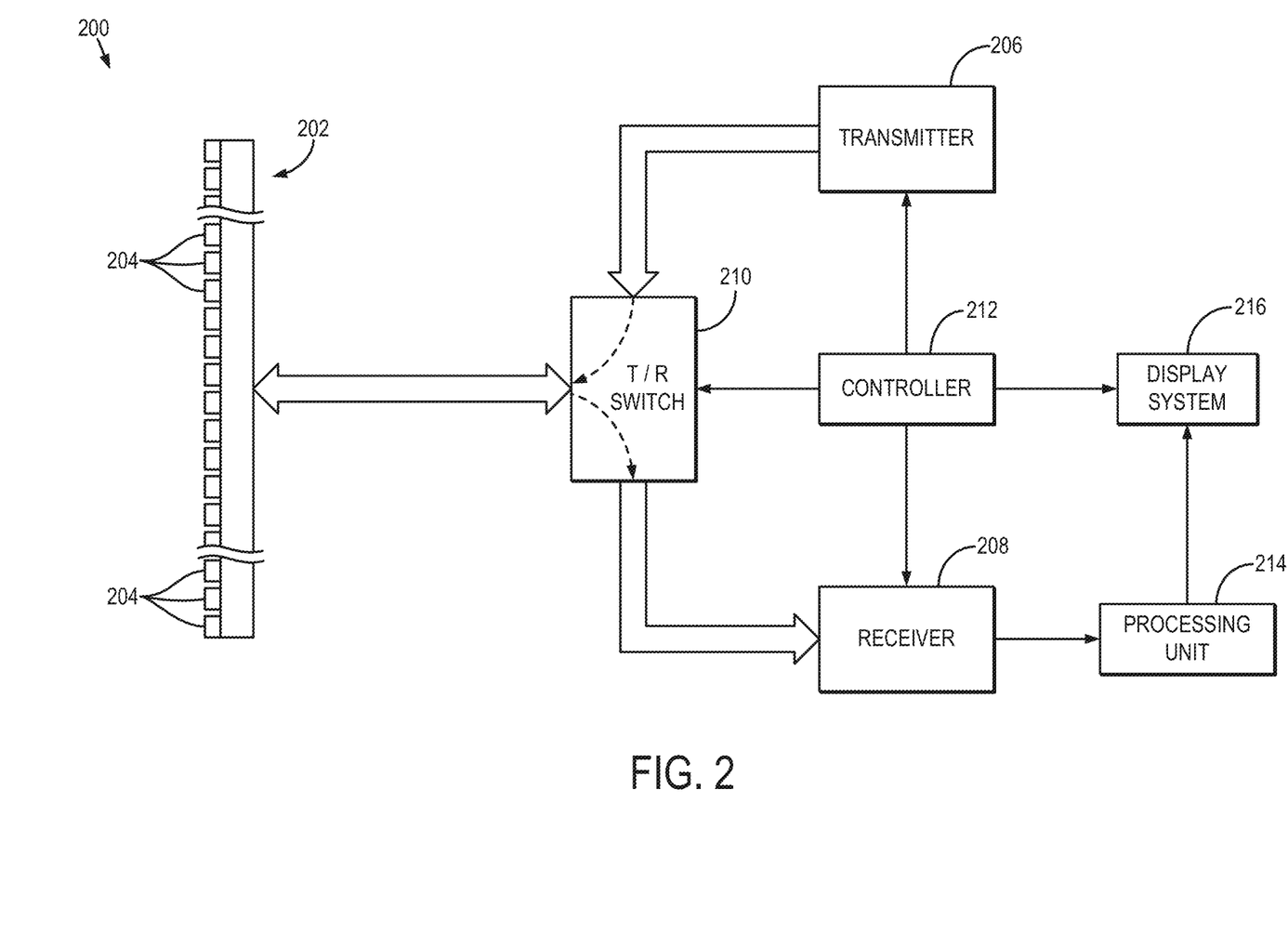
FIG. 2 shows a block diagram of an example ultrasound system that can implement the methods described in the present disclosure.

Referring to FIG. 2, an example of an ultrasound system 200 that can implement the methods described in the present disclosure is shown. The ultrasound system 200 includes a transducer array 202 that includes a plurality of separately driven transducer elements 204. The transducer array 202 can include any suitable ultrasound transducer array, including linear arrays, curved arrays, phased arrays, and so on. Similarly, the transducer array 202 can include a 1D transducer, a 1.5D transducer, a 1.75D transducer, a 2D transducer, a 3D transducer, and so on.

When energized by a transmitter 206, a given transducer element 204 produces a burst of ultrasonic energy. The ultrasonic energy reflected back to the transducer array 202 (e.g., an echo) from the object or subject under study is converted to an electrical signal (e.g., an echo signal) by each transducer element 204 and can be applied separately to a receiver 208 through a set of switches 210. The transmitter 206, receiver 208, and switches 210 are operated under the control of a controller 212, which may include one or more processors. As one example, the controller 212 can include a computer system.

The transmitter 206 can be programmed to transmit unfocused or focused ultrasound waves. In some configurations, the transmitter 206 can also be programmed to transmit diverged waves, spherical waves, cylindrical waves, plane waves, or combinations thereof. Furthermore, the transmitter 206 can be programmed to transmit spatially or temporally encoded pulses.

The receiver 208 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 206 and the receiver 208 can be programmed to implement a high frame rate. For instance, a frame rate associated with an acquisition pulse repetition frequency ("PRF") of at least 100 Hz can be implemented. In some configurations, the ultrasound system 200 can sample and store at least one hundred ensembles of echo signals in the temporal direction.

The controller 212 can be programmed to design or otherwise select an imaging sequence using techniques described in the present disclosure, or as otherwise known in the art. In some embodiments, the controller 212 receives user inputs defining various factors used in the design of the imaging sequence.

A scan can be performed by setting the switches 210 to their transmit position, thereby directing the transmitter 206 to be turned on momentarily to energize transducer elements 204 during a single transmission event according to the selected imaging sequence. The switches 210 can then be set to their receive position and the subsequent echo signals produced by the transducer elements 204 in response to one or more detected echoes are measured and applied to the receiver 208. The separate echo signals from the transducer elements 204 can be combined in the receiver 208 to produce a single echo signal.

The echo signals are communicated to a processing unit 214, which may be implemented by a hardware processor and memory, to process echo signals or images generated from echo signals. As an example, the processing unit 214 can generate IHC biomarkers using the methods described in the present disclosure. Images produced from the echo signals by the processing unit 214 can be displayed on a display system 216.

In a non-limiting example, a prospective study was conducted with women volunteers who had suspicious breast masses and scheduled for breast biopsy. Shear wave acquisition was performed before biopsy. Of those who underwent biopsy, 258 biopsy-proven invasive breast cancers patients (age range: 27-89 years, mean age: 62.1±12.4 years, median age: 63 years) with 261 malignant masses were included Breast ultrasound examinations were performed by a skilled sonographer with experience in breast ultrasound. The GE LOGIQ E9 ultrasound clinical scanner (GE Healthcare, Wauwatosa, WI), equipped with a 9L-D linear array probe (GE Healthcare, Wauwatosa, WI) with frequency range between 2-8 MHz, was used for SWE data acquisition. The B-mode imaging was first used to find the location of the breast lesion. Then the machine was switched to SWE mode for SWE measurement. Three to five images were obtained from each lesion. Later, one of the members from the investigative team chose one of the most consistent images to draw regions of interest (ROI). According to the lesion size, one to three 3 mm$^2$ ROIs were obtained inside the mass. The mean shear wave speed (SWS), maximum SWS, minimum SWS and standard deviation of the SWS inside each ROI were calculated by the ultrasound machine. The measured SWS was also converted to the elasticity in unit of kilopascal.

Mass size d was recorded as the greatest dimension of the tumor shown on the B-mode image. Presence of calcifications was read from the breast mammographic examination. Axillary lymph node (ALN) status, histological type and grade were obtained from biopsies. IHC biomarkers ER, PR, HER2 and Ki-67 were performed on the non-decalcified paraffin embedded specimens, which were obtained from core biopsy. Reporting criteria for ER and PR status was based on less than 1% reactive cells was negative and greater than or equal to 1% reactive cells was positive. IHC staining for HER2 was scored according to standard criteria as 0, 1+, 2+ or 3+. Score of 0 and 1+ were considered as negative and score of 3+ was considered as positive. Fluorescence in situ hybridization for HER2 amplification was performed when HER2 score was 2+. Positive fluorescence in situ hybridization amplification was considered as HER2 positive. The histological grade was determined.

Figure 3:
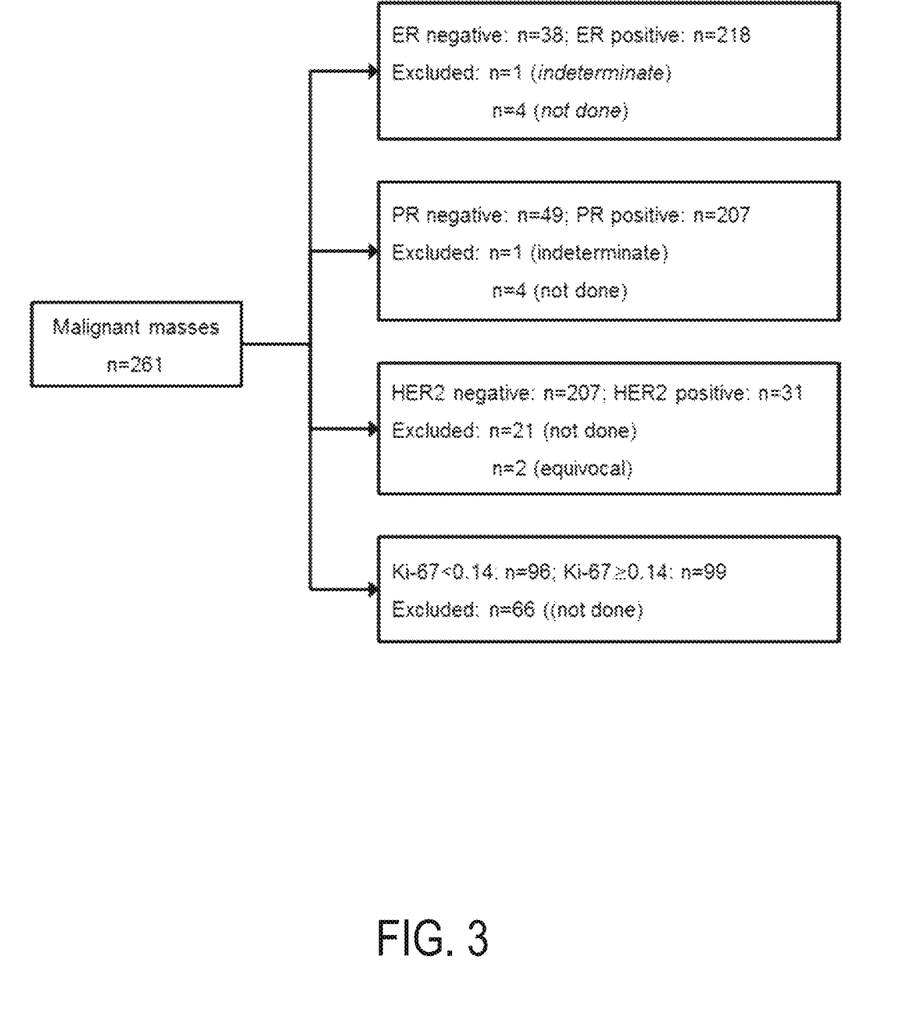
FIG. 3 is a block diagram of non-limiting example immunohistochemical results.

Referring to FIG. 3, the non-limiting example IHC results for the 261 lesions are summarized. Based on the four IHC biomarkers, the cancers were divided into five molecular subtypes: Luminal A—ER positive, PR positive/negative, HER2 negative, Ki-67<14%; Luminal B (without HER2 overexpression)—ER positive, PR positive/negative, HER2 negative, and Ki-67≥14%; Luminal B-like (with HER2 overexpression)—ER positive, PR positive/negative, HER2 positive, any Ki-67; HER2 positive—ER negative and PR negative, HER2 positive; Triple-negative (TN)—ER negative, PR negative and HER2 negative.

Statistical analysis was conducted with RStudio (RStudio, PBC, Boston, MA) and it was performed on the SWE parameters measured on the ROIs. The relationship between the SWE parameters and each prognostic factor was evaluated. Differences were deemed to be statistically significant if p value was 0.05 or less. ROC curve analysis was used to determine the optimal cutoff values, as well as the corresponding sensitivity and specificity. The optimal cut-point was defined as the point with maximum specificity while keeping sensitivity more than 80%. To further correlate the SWE measurement with prognostic factors, a shear wave parameter of mass characteristic frequency, denoted by (mass, was used, which is defined as the ratio of the minimum shear wave speed (SWS) to the mass size.

Table 2 below summarizes the relationship between SWE parameters ($E_{mean}$, $E_{max}$, $E_{min}$, $E_{sd}$ and $f_{mass}$) and histologic features in the non-limiting example. Significant differences were found for $E_{mean}$, $E_{max}$, $E_{min}$ and $E_{sd}$ among different invasive mass size groups (p<0.001). High shear wave elasticity was associated with large invasive mass size. No significant difference was found for SWE elasticity for the lesions with or without calcification presence. High $E_{mean}$ was associated with positive lymph node status (p=0.001) and high histological grade (p=0.04). High $E_{max}$ was also associated with positive lymph node status (p=0.001) and high histological grade (p=0.04). High $E_{sd}$ was associated with positive lymph node status (p=0.02). Low $f_{mass}$ was associated with calcification presence (p<0.001), positive lymph node status (p=0.01), and high histological grade (p=0.002).

TABLE 2

Summary of the Relationship between Non-Limiting Example Shear Wave Elastography Parameters and Histologic Parameters

| SWE parameters | $E_{mean}$ ± SD (kPa) | $E_{max}$ ± SD (kPa) | $E_{min}$ ± SD (kPa) | $E_{sd}$ ± SD (kPa) | $f_{mass}$ ± SD (Hz) |
| --- | --- | --- | --- | --- | --- |
| Tumor size | | | | | |
| P value | <0.001* | <0.001* | <0.001* | <0.001* | ND |
| ≤10 mm (85) | 61.8 ± 37.6 | 118.9 ± 68.5 | 25.4 ± 19.0 | 1.8 ± 1.3 | 35.3 ± 16.6 |
| 10-20 mm(101) | 85.8 ± 35.5 | 166.9 ± 57.0 | 32.3 ± 21.4 | 2.7 ± 1.7 | 22.1 ± 8.4 |
| >20 mm (75) | 99.6 ± 33.4 | 192.0 ± 51.5 | 41.8 ± 26.3 | 3.0 ± 1.7 | 12.6 ± 5.2 |
| Calcifications | | | | | |
| P value | 0.46 | 0.56 | 0.17 | 0.30 | <0.001* |
| None(169) | 84.0 ± 39.0 | 157.9 ± 64.1 | 34.2 ± 23.1 | 2.4 ± 1.5 | 25.1 ± 13.2 |
| Present(92) | 79.0 ± 37.6 | 160.4 ± 68.9 | 31.2 ± 24.8 | 2.7 ± 1.9 | 20.6 ± 15.9 |
| Lymph node | | | | | |
| P value | 0.001* | <0.001* | 0.06 | 0.02* | 0.01* |
| Negative (210) | 78.5 ± 38.3 | 151.9 ± 66.0 | 31.5 ± 22.6 | 2.4 ± 1.6 | 23.9 ± 12.7 |
| Positive (51) | 97.5 ± 35.8 | 187.4 ± 56.6 | 39.7 ± 27.1 | 2.9 ± 1.6 | 22.0 ± 19.7 |

TABLE 2-continued

Summary of the Relationship between Non-Limiting Example Shear Wave Elastography Parameters and Histologic Parameters

| SWE parameters | $E_{mean}$ ± SD (kPa) | $E_{max}$ ± SD (kPa) | $E_{min}$ ± SD (kPa) | $E_{sd}$ ± SD (kPa) | $f_{mass}$ ± SD (Hz) |
|---|---|---|---|---|---|
| Subtype | | | | | |
| P value | 0.005* | 0.008* | 0.02* | 0.12 | 0.73 |
| IDC (164) | 80.8 ± 37.8 | 157.0 ± 66.1 | 32.1 ± 23.7 | 2.6 ± 1.8 | 23.0 ± 12.8 |
| IMC (45) | 90.7 ± 36.4 | 173.2 ± 54.7 | 37.3 ± 23.3 | 2.5 ± 1.4 | 26.4 ± 18.6 |
| ILC (32) | 93.5 ± 36.6 | 177.7 ± 61.6 | 39.6 ± 23.3 | 2.6 ± 1.5 | 22.6 ± 13.3 |
| DCIS (15) | 56.9 ± 43.7 | 106.3 ± 75.3 | 24.3 ± 22.7 | 1.5 ± 1.1 | 23.3 ± 18.0 |
| NMC (5) | 57.2 ± 36.1 | 127.1 ± 62.1 | 16.2 ± 18.5 | 2.5 ± 1.2 | 20.0 ± 15.3 |
| Histological grade | | | | | |
| P value | 0.04* | 0.04* | 0.46 | 0.25 | 0.002* |
| I/II(177) | 81.1 ± 37.0 | 157.3 ± 63.7 | 32.9 ± 22.6 | 2.5 ± 1.6 | 25.3 ± 14.9 |
| III(61) | 92.6 ± 38.4 | 175.8 ± 63.0 | 36.9 ± 26.3 | 2.8 ± 1.9 | 19.2 ± 10.4 |

For Table 2, the numbers in parentheses are mass numbers. SD indicates standard deviation. IDC indicates invasive ductal carcinoma; IMC indicates invasive mammary carcinoma; ILC indicates invasive lobular carcinoma; DCIS indicates ductal carcinoma in situ; NMC indicates non-mammary carcinoma. ND indicates not done. *p<0.05 represents a difference that is statistically significant.

Figure 4:
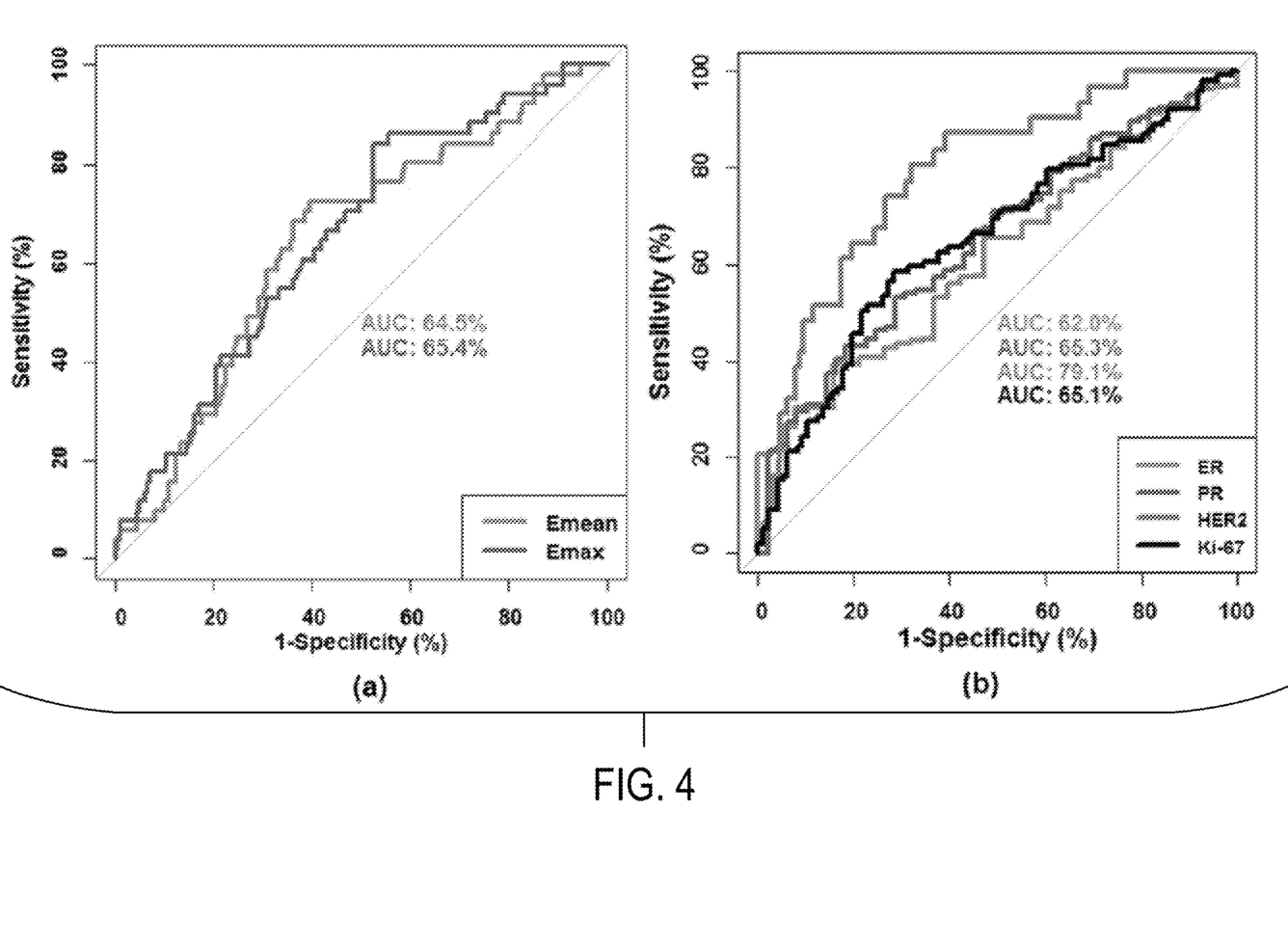
FIG. 4 shows graphs of non-limiting example ROC curves of mean elasticity ($E_{mean}$) and maximum elasticity ($E_{max}$) for diagnosing ALN status, and ROC curves of mass characteristic frequency ($f_{mass}$) for diagnosing IHC biomarker (ER, PR, HER2 and Ki-67) status.

Referring to FIG. 4, non-limiting example ROC curves of mean elasticity ($E_{mean}$) and maximum elasticity ($E_{max}$) for diagnosing ALN status, and ROC curves of mass characteristic frequency ($f_{mass}$) for diagnosing IHC biomarker (ER, PR, HER2 and Ki-67) status, are shown. ROC indicates receiver operating characteristic. ER indicates estrogen receptor status. PR indicates progesterone receptor. HER2 indicates human epidermal growth factor receptor 2. In the non-limiting example, the ROC curve analysis of the lymph node status yielded cutoff values of $E_{mean}$ at 69.8 kPa, with a sensitivity of 80.4% and a specificity of 41.0%; of $E_{max}$ at 156.7 kPa, with a sensitivity of 84.3% and a specificity of 47.6%.

There were five breast cancer types were included, including 164 (62.8%) invasive ductal carcinomas, 45 (17.2%) invasive mammary carcinomas, 32 (12.3%) invasive lobular carcinoma, 15 (5.8%) ductal carcinomas in situ and 5 (1.9%) non-mammary carcinoma. Statistically significant differences were found for $E_{mean}$, $E_{max}$ and $E_{min}$ among different breast cancer types. Invasive lobular carcinoma showed the highest stiffness among the five types. The stiffness of ductal carcinomas in situ and non-mammary carcinoma was lower than that of the invasive breast carcinomas.

Table 3 below summarizes the correlation between shear wave elasticity and IHC biomarkers for the non-limiting example. Significant difference was found for $E_{max}$ among different HER2 statuses (p=0.01). Also, significant differences were found for $E_{sd}$ among different HER2 statuses (p<0.001) and IHC subtypes (p=0.01). Positive ER, positive PR, high Ki-67 (≥14%) tended to have high stiffness and strong stiffness heterogeneity. Mass characteristic frequency was found significantly correlated with ER status, PR status, HER2 status, Ki-67, as well as the IHC subtypes. As shown in Table 3, negative ER, negative PR, positive HER2 status and higher Ki-67 (<14%) were significantly associated with lower $f_{mass}$. The ROC curve analysis yielded cutoff values of $f_{mass}$ at: 12.9 Hz for ER, with a sensitivity of 80.3% and a specificity of 29.0%; 13.2 Hz for PR, with a sensitivity of 80.2% and a specificity of 36.7%; 17.4 Hz for HER2, with a sensitivity of 80.6% and a specificity of 68.1%; 30.4 Hz for Ki-67, with a sensitivity of 80.8% and a specificity of 36.5%. Significant difference was also found among different IHC subtypes. Luminal A and Luminal B types exhibited higher averaged $f_{mass}$ values than other IHC subtypes.

TABLE 3

Summary of the Relationship between Non-Limiting Example Shear Wave Elastography Parameters and IHC Parameters

| SWE parameters | $E_{mean}$ ± SD (kPa) | $E_{max}$ ± SD (kPa) | $E_{min}$ ± SD (kPa) | $E_{sd}$ ± SD (kPa) | $f_{mass}$ ± SD (Hz) |
|---|---|---|---|---|---|
| ER | | | | | |
| P value | 0.58 | 0.54 | 0.33 | 0.87 | 0.02* |
| Negative(38) | 79.9 ± 36.3 | 154.3 ± 64.0 | 30.9 ± 24.1 | 2.5 ± 1.8 | 18.1 ± 8.2 |
| Positive(218) | 83.2 ± 38.9 | 161.0 ± 66.1 | 33.8 ± 23.7 | 2.5 ± 1.6 | 24.3 ± 14.9 |
| PR | | | | | |
| P value | 0.22 | 0.42 | 0.10 | 0.94 | <0.001* |
| Negative(49) | 77.1 ± 34.3 | 154.3 ± 64.0 | 29.0 ± 22.3 | 2.5 ± 1.8 | 19.0 ± 16.8 |
| Positive(207) | 84.1 ± 39.3 | 160.7 ± 66.1 | 34.4 ± 24.0 | 2.5 ± 1.6 | 24.4 ± 13.4 |
| HER2 | | | | | |
| P value | 0.99 | 0.01* | 0.32 | <0.001* | <0.001* |
| Negative(207) | 84.7 ± 39.1 | 159.2 ± 64.5 | 34.9 ± 24.6 | 2.4 ± 1.6 | 25.0 ± 14.2 |
| Positive(31) | 83.8 ± 23.9 | 189.5 ± 45.6 | 28.0 ± 15.8 | 3.6 ± 1.9 | 13.4 ± 7.4 |

TABLE 3-continued

Summary of the Relationship between Non-Limiting Example
Shear Wave Elastography Parameters and IHC Parameters

| SWE parameters | $E_{mean} \pm SD$ (kPa) | $E_{max} \pm SD$ (kPa) | $E_{min} \pm SD$ (kPa) | $E_{sd} \pm SD$ (kPa) | $f_{mass} \pm SD$ (Hz) |
|---|---|---|---|---|---|
| Ki-67 | | | | | |
| P value | 0.18 | 0.21 | 0.45 | 0.48 | <0.001* |
| <14%(96) | 80.7 ± 39.7 | 156.3 ± 65.3 | 33.0 ± 22.5 | 2.4 ± 1.5 | 27.1 ± 12.8 |
| ≥14%(99) | 88.3 ± 36.8 | 168.3 ± 63.3 | 36.2 ± 25.1 | 2.7 ± 1.8 | 21.2 ± 12.3 |
| IHC subtype | | | | | |
| P value | 0.43 | 0.11 | 0.40 | 0.01* | <0.001* |
| Luminal A(93) | 82.6 ± 38.6 | 158.8 ± 63.4 | 33.9 ± 22.3 | 2.4 ± 1.5 | 27.5 ± 12.7 |
| Luminal B(70) | 88.9 ± 40.3 | 165.0 ± 67.1 | 36.9 ± 26.6 | 2.6 ± 1.8 | 22.8 ± 13.0 |
| Luminal B-like(23) | 89.9 ± 21.8 | 197.4 ± 39.9 | 31.1 ± 15.8 | 3.5 ± 1.7 | 13.6 ± 6.8 |
| HER2+(6) | 64.6 ± 24.8 | 162.2 ± 65.4 | 18.8 ± 13.7 | 3.9 ± 2.8 | 12.6 ± 8.8 |
| TN(22) | 82.5 ± 39.3 | 149.0 ± 72.6 | 32.1 ± 23.1 | 2.2 ± 1.7 | 19.5 ± 8.1 |

In Table 3, SD indicates standard deviation. The numbers in parenthesis are the mass numbers. IHC indicates immunohistochemical; ER indicates estrogen receptor status; PR indicates progesterone receptor; HER2 indicates human epidermal growth factor receptor 2; TN indicates triple negative. *p<0.05 represents a difference that is statistically significant.

Table 4 below summarizes the non-limiting example mass characteristic frequency values in different IHC subtypes. There were 93 (43.5%) Luminal A cancers, 70 (32.7%) Luminal B cancers, 23 (10.8%) Luminal B-like cancers, 6 (2.8%) HER2+ cancers and 22 (10.3%) TN cancers. Among them, most of the Luminal A type (97.9%) and Luminal B type (72.9%) cancers were with Grade I/II, while most of the more aggressive types, like Luminal B-like (52.4%), HER2+ (66.7%) and TN (81.0%) type cancers were with Grade III. For all IHC subtypes, low averaged $f_{mass}$ was correlated with high histological grade and positive lymph node status.

TABLE 4

Summary of Non-limiting Example Mass Characteristic
Frequency in Different IHC Subtypes

| IHC subtype | Luminal A | Luminal B | Luminal B-like | HER2+ | TN |
|---|---|---|---|---|---|
| Grade | | | | | |
| I/II | 27.7 ± 12.7(91) | 22.5 ± 12.8(51) | 12.8 ± 6.3 (10) | 19.3 ± 14.7(2) | 24.1 ± 7.3(4) |
| III | 18.7 ± 1.5(2) | 23.4 ± 13.9(19) | 15.5 ± 7.2(11) | 9.2 ± 3.5 (4) | 18.6 ± 8.4(17) |
| Lymph node | | | | | |
| Negative | 27.6 ± 12.3(86) | 22.7 ± 12.1(48) | 15.6 ± 7.6(13) | 12.9 ± 11.3(4) | 20.1 ± 7.7(19) |
| Positive | 27.3 ± 17.8(7) | 22.9 ± 15.0(22) | 10.9 ± 4.6 (10) | 12.0 ± 1.7(2) | 15.8 ± 11.9(3) |

The data in Table 4 are represented as mean±standard deviation in Hz. The numbers in parentheses are the mass numbers. TN indicates triple negative; IHC indicates immunohistochemical.

A difference was found for $E_{max}$ among different HER2 statuses. A difference was also found for $E_{sd}$ among different HER2 statuses and different IHC subtypes. $f_{mass}$ was correlated with the presence of calcifications, lymph node status, histological grade, statuses of IHC biomarkers, as well as the IHC subtypes.

In a non-limiting example, negative ER, negative PR, positive HER2 status and higher Ki-67 (<14%) were associated with lower $f_{mass}$ values. Different $f_{mass}$ values were found among different IHC subtypes, and luminal B with HER2+ and HER2+ groups was associated with lower $f_{mass}$ values.

The present disclosure has described one or more preferred embodiments, and it should be appreciated that many equivalents, alternatives, variations, and modifications, aside from those expressly stated, are possible and within the scope of the invention.

The invention claimed is:

1. A method for determining a presence of an immunohistochemical (IHC) biomarker in a region of interest of a subject, comprising:
   accessing shear wave data acquired from the region of interest of the subject using an ultrasound imaging system, wherein the shear wave data comprise shear wave speed data;
   determining a minimum shear wave speed from the shear wave speed data;
   accessing image data from the region of interest of the subject, wherein the image data comprise at least one image of the region of interest of the subject;
   determining a physical parameter of the region of interest from the image data;
   determining a mass characteristic frequency based on a ratio of the determined minimum shear wave speed and the determined physical parameter of the region of interest;
   determining a threshold value of mass characteristic frequency by identifying a point on a receiver operating characteristic (ROC) curve of mass characteristic frequency values associated with the IHC biomarker, wherein the point has a maximum specificity on the ROC curve while keeping sensitivity over 80%;

determining the presence of the IHC biomarker in the region of interest by comparing the mass characteristic frequency to the threshold value, wherein the IHC biomarker is determined to be present in the region of interest when the mass characteristic frequency meets a threshold value criteria based on the threshold value; and generating a report, wherein the report indicates whether the IHC biomarker is present in the region of interest based on the determined presence of the IHC biomarker.

2. The method of claim 1, wherein the IHC biomarker comprises a plurality of IHC biomarkers and determining the presence of the IHC biomarker comprises determining the presence of the plurality of IHC biomarkers in the region of interest by comparing the mass characteristic frequency to each of a plurality of threshold values, wherein each of the plurality of threshold values is associated with a different one of the plurality of IHC biomarkers;

wherein each of the plurality of threshold values is determined by identifying a point on an ROC curve of mass characteristic frequency values associated with each of the respective plurality of IHC biomarkers, wherein the point has a maximum specificity on the ROC curve while keeping sensitivity over 80%;

wherein each of the plurality of IHC biomarkers is determined to be present in the region of interest when the mass characteristic frequency meets a separate threshold value criteria based on each of the plurality of threshold values; and wherein the report indicates whether each of the plurality of IHC biomarkers is present in the region of interest based on the determined presence of each of the plurality of IHC biomarkers.

3. The method of claim 1, wherein the physical parameter of the region of interest is a size of the region of interest.

4. The method of claim 1, wherein the region of interest is at least one of a mass, tumor, lesion, breast mass, breast tumor, breast lesion, or breast cancer.

5. The method of claim 4, wherein the physical parameter is a greatest dimension of the region of interest shown in the image data.

6. The method of claim 4, wherein the IHC biomarker is at least one of estrogen receptor (ER), progesterone receptor (PR), human epidermal growth factor receptor 2 (HER2), or proliferation marker Ki-67.

7. The method of claim 6, wherein a plurality of threshold values of the mass characteristic frequency distinguish between the at least one of ER, PR, HER2, or Ki-67 biomarkers.

8. The method of claim 1, further comprising determining at least one of a mass transit time as an inverse of the mass characteristic frequency or a square root of the mass characteristic frequency.

9. The method of claim 1, wherein the image data includes ultrasound B-mode image data.

10. A system for determining a presence of an immunohistochemical (IHC) biomarker in a region of interest of a subject, comprising:

an ultrasound imaging system configured to acquire image data and shear wave data from the region of interest of the subject, wherein the shear wave data comprises shear wave speed data and the image data comprise at least one image of the region of interest;

a computer system configured to:
i) access the acquired shear wave data acquired from the region of interest of the subject;
ii) determine a minimum shear wave speed from the shear wave speed data;
iii) access the image data from the region of interest of the subject;
iv) determine a physical parameter of the region of interest from the image data;
v) determine a mass characteristic frequency based on a ratio of the determined minimum shear wave speed and the determined physical parameter of the region of interest;
vi) determine a presence of the IHC biomarker by comparing the mass characteristic frequency to a threshold value associated with the IHC biomarker, wherein the threshold value is determined by identifying a point on a receiver operating characteristic (ROC) curve of mass characteristic frequency values associated with the IHC biomarker, wherein the point has a maximum specificity on the ROC curve while keeping sensitivity over 80%; and
vii) generate a report, wherein the report indicates whether the IHC biomarker is present in the region of interest based on the determined presence of the IHC biomarker.

11. The system of claim 10, wherein the IHC biomarker comprises a plurality of IHC biomarkers and the computer system is further configured to determine the presence of the plurality of IHC biomarkers in the region of interest by comparing the mass characteristic frequency to each of a plurality of threshold values, wherein each of the plurality of threshold values is associated with a different one of the plurality of IHC biomarkers;

wherein each of the plurality of threshold values is determined by identifying a point on an ROC curve of mass characteristic frequency values associated with each of the respective plurality of IHC biomarkers that has maximum specificity while keeping sensitivity over 80%;

wherein each of the plurality of IHC biomarkers is determined to be present in the region of interest when the mass characteristic frequency meets a separate threshold value criteria based on each of the plurality of threshold values; and wherein the report indicates whether each of the plurality of IHC biomarkers is present in the region of interest based on the determined presence of each of the plurality of IHC biomarkers.

12. The system of claim 10, wherein the physical parameter of the region of interest is a size of the region of interest.

13. The system of claim 10, wherein the region of interest is at least one of a mass, tumor, lesion, breast mass, breast tumor, breast lesion, or breast cancer.

14. The system of claim 13, wherein the physical parameter is a greatest dimension of the tumor shown in the image data.

15. The system of claim 13, wherein the IHC biomarker is at least one of estrogen receptor (ER), progesterone receptor (PR), human epidermal growth factor receptor 2 (HER2), or proliferation marker Ki-67.

16. The system of claim 15, wherein a plurality of threshold values of the mass characteristic frequency distinguish between the at least one of ER, PR, HER2, or Ki-67 biomarkers.

17. The system of claim 10, wherein the computer system is further configured to determine at least one of a mass transit time as an inverse of the mass characteristic frequency or a square root of the mass characteristic frequency.

18. The system of claim 10, wherein the image data includes ultrasound B-mode image data.

19. A method for determining a response to chemotherapy treatment in a region of interest of a subject, comprising:
  accessing first shear wave data acquired from the region of interest of the subject using an ultrasound imaging system, wherein the first shear wave data comprise first shear wave speed data acquired before administration of the chemotherapy treatment;
  determining a first minimum shear wave speed from the first shear wave speed data;
  accessing first image data from the region of interest of the subject, wherein the first image data comprise at least one image of the region of interest acquired before administration of the chemotherapy treatment;
  determining a first physical parameter of the region of interest from the first image data;
  determining a first mass characteristic frequency based on a ratio of the determined first minimum shear wave speed and the determined first physical parameter of the region of interest;
  accessing second shear wave data acquired from the region of interest of the subject using the ultrasound imaging system, wherein the second shear wave data comprise second shear wave speed data acquired after administration of the chemotherapy treatment;
  determining a second minimum shear wave speed from the second shear wave speed data;
  accessing second image data from the region of interest of the subject, wherein the second image data comprise at least one image of the region of interest acquired after administration of the chemotherapy treatment;
  determining a second physical parameter of the region of interest from the second image data;
  determining a second mass characteristic frequency based on a ratio of the determined second minimum shear wave speed and the determined second physical parameter of the region of interest; and
  determining the response to the chemotherapy treatment in the region of interest by:
  computing a mass characteristic frequency change value as a change from the first mass characteristic frequency to the second mass characteristic frequency; and
  comparing the change to a threshold value; and
  generating a report of the response to chemotherapy treatment in the region of interest, wherein the report indicates discontinuing the chemotherapy treatment when the mass characteristic frequency change exceeds the threshold value.

20. The method of claim 1, wherein the IHC biomarker is at least one of estrogen receptor (ER), progesterone receptor (PR), human epidermal growth factor receptor 2 (HER2), or proliferation marker Ki-67; and wherein:
  when the IHC biomarker is ER, the IHC biomarker is determined to be present in the region of interest when the mass characteristic frequency is at or above the threshold value;
  when the IHC biomarker is PR, the IHC biomarker is determined to be present in the region of interest when the mass characteristic frequency is at or above the threshold value;
  when the IHC biomarker is HER2, the IHC biomarker is determined to be present in the region of interest when the mass characteristic frequency is below the threshold value; and
  when the IHC biomarker is Ki-67, the IHC biomarker is determined to be present in the region of interest when the mass characteristic frequency is below the threshold value.

21. The system of claim 10, wherein the IHC biomarker is at least one of estrogen receptor (ER), progesterone receptor (PR), human epidermal growth factor receptor 2 (HER2), or proliferation marker Ki-67; and wherein:
  when the IHC biomarker is ER, the IHC biomarker is determined to be present in the region of interest when the mass characteristic frequency is at or above the threshold value;
  when the IHC biomarker is PR, the IHC biomarker is determined to be present in the region of interest when the mass characteristic frequency is at or above the threshold value;
  when the IHC biomarker is HER2, the IHC biomarker is determined to be present in the region of interest when the mass characteristic frequency is below the threshold value; and
  when the IHC biomarker is Ki-67, the IHC biomarker is determined to be present in the region of interest when the mass characteristic frequency is below the threshold value.

* * * * *

UNITED STATES PATENT AND TRADEMARK OFFICE
CERTIFICATE OF CORRECTION

| | | |
|---|---|---|
| PATENT NO. | : 12,097,075 B2 | Page 1 of 1 |
| APPLICATION NO. | : 17/466073 | |
| DATED | : September 24, 2024 | |
| INVENTOR(S) | : Azra Alizad et al. | |

It is certified that error appears in the above-identified patent and that said Letters Patent is hereby corrected as shown below:

In the Specification

Column 12, Line 26-27, "by (mass," should be --by $f_{mass}$,--.

Signed and Sealed this
Twenty-sixth Day of November, 2024

Katherine Kelly Vidal
*Director of the United States Patent and Trademark Office*